United States Patent
Raupach

(10) Patent No.: US 7,403,597 B2
(45) Date of Patent: Jul. 22, 2008

(54) RADIATION DIAPHRAGM IN DEVICE HAVING TWO DIAPHRAGMS, AND METHOD FOR SCANNING A SUBJECT THEREWITH

(75) Inventor: Rainer Raupach, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 61 days.

(21) Appl. No.: 11/409,141

(22) Filed: Apr. 21, 2006

(65) Prior Publication Data

US 2006/0262897 A1 Nov. 23, 2006

(30) Foreign Application Priority Data

Apr. 22, 2005 (DE) ................. 10 2005 018 811

(51) Int. Cl.
*G21K 1/00* (2006.01)
*G21K 1/02* (2006.01)
*G21K 1/04* (2006.01)

(52) U.S. Cl. ............... 378/145; 378/147; 378/150

(58) Field of Classification Search ............. 378/4, 378/16, 15, 19, 147–153, 160, 145
See application file for complete search history.

(56) References Cited

U.S. PATENT DOCUMENTS

| | | | | |
|---|---|---|---|---|
| 4,464,778 A | | 8/1984 | Goldmann | |
| 5,237,599 A | * | 8/1993 | Gunji et al. | 378/148 |
| 6,320,929 B1 | * | 11/2001 | Von Der Haar | 378/4 |
| 6,359,958 B2 | * | 3/2002 | Toth | 378/19 |
| 6,418,183 B1 | * | 7/2002 | Fox et al. | 378/15 |
| 7,170,975 B2 | * | 1/2007 | Distler et al. | 378/150 |
| 7,209,547 B2 | * | 4/2007 | Baier et al. | 378/149 |
| 2006/0050841 A1 | | 3/2006 | Distler et al. | |

FOREIGN PATENT DOCUMENTS

DE 42 29 321 3/1994
DE 196 25 864 10/1999

* cited by examiner

*Primary Examiner*—Irakli Kiknadze
(74) *Attorney, Agent, or Firm*—Schiff Hardin LLP

(57) ABSTRACT in a diaphragm device for an x-ray apparatus for scanning a subject with a radiation beam and a scanning method using such a diaphragm device, the diaphragm device has at least two diaphragms. For at least one segment of the scan, the radiation beam that has been adjusted with the first diaphragm can be at least partially dynamically masked by the second diaphragm. High adjustment precisions for precise exposure of a measurement field of detector and high adjustment speed for masking of a radiation beam that is not needed for reconstruction of an image, or for reduction of a radiation exposure of the subject can be implemented to equal degree with the two diaphragms that are separate from one another.

26 Claims, 4 Drawing Sheets

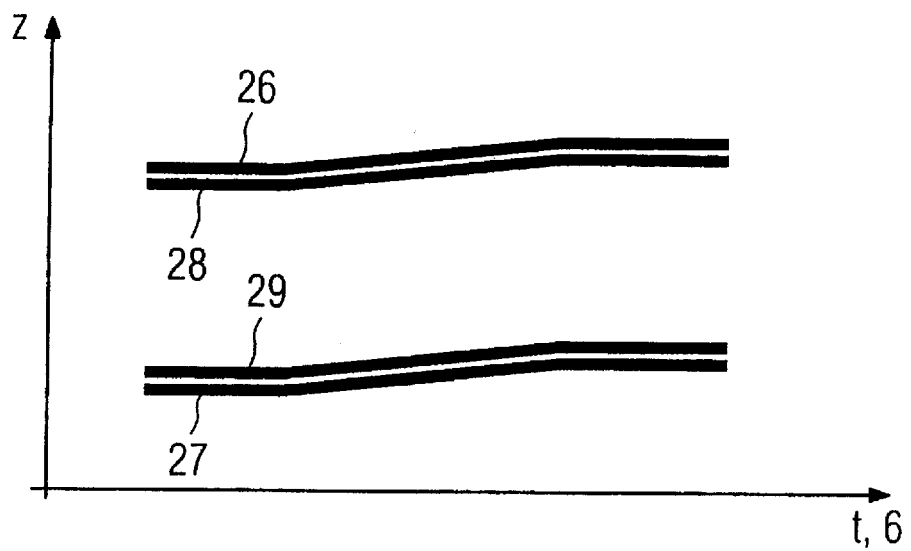

RADIATION DIAPHRAGM IN DEVICE HAVING TWO DIAPHRAGMS, AND METHOD FOR SCANNING A SUBJECT THEREWITH

BACKGROUND OF THE INVENTION

1. Field of the Invention

The present invention concerns a diaphragm device for an x-ray apparatus that is provided for scanning a subject, and a method for scanning a subject with such a diaphragm device.

2. Description of the Prior Art

A diaphragm device is known from DE 102 42 920 A1 with which the radiation beam can be adjusted in a very precise manner on the measurement field of the detector to avoid an unnecessary radiation exposure given a scanning of a subject with an x-ray apparatus, for example in the form of a computed tomography apparatus. To adjust the radiation beam emanating from the x-ray radiator, the diaphragm device has a diaphragm with two beam-proximate absorber elements. The diaphragm is fashioned such that both absorber elements can be positioned (set) with a high adjustment precision before the beginning of an examination.

Given a helical scan of a subject in which the acquisition system rotates around a system axis of the computed tomography apparatus and with the subject being simultaneously displaced relative to the acquisition system in the direction of the system axis, for reconstruction of an image within a usable volume it is necessary to irradiate a scan volume that is larger in the direction of the system axis than the usable volume. The larger (in comparison to the usable volume) scan volume significantly depends on the algorithm used for reconstruction of the image. the total irradiated volume results from usable volume itself (defined by the reconstruction algorithm that will be used) plus a number of additionally-required rotations, or the additionally required fraction of a rotation that must be implemented during a leading or advance movement and a trailing movement of the x-ray radiator. Only a fraction of the information acquired during the leading movement and trailing movement, however is used later for reconstruction, such that the subject is exposed to an unnecessary radiation exposure during these segments of the scan.

With increasing volume coverage of the detectors in the direction of the system axis, the number of the rotations of the acquisition system for scanning the usable volume can in fact be reduced, but the number of the rotations of a spiral scan during the leading and trailing movements that are necessary for complete reconstruction of the usable volume remain unaffected by the volume coverage of the detector. As a consequence, the proportion of the rotations due to the leading and the trailing movement thus increases in comparison to the rotations that are required for the total scanning. The dose efficiency, thus the actual proportion of the radiation used for reconstruction, is thus simultaneously reduced.

For example, in a computed tomography apparatus having a detector with $Z=16$ lines and a line width of $B=0.75$ mm and an x-ray radiator that radiates the 12 mm-wide measurement field in the direction of the system axis of the computed tomography apparatus with a radiation beam adjusted (gated) by a diaphragm device, the proportion of the scan due to the leading -and the trailing movement in comparison to the total scan of the sample volume amounts to 12%, given a usable volume to be scanned of $L=200$ mm, a set pitch of $P=1$ and given one full rotation of the acquisition system required for reconstruction during each of the leading movement and the trailing movement of the scan. Only approximately half of the radiation applied during the leading and trailing movement contributes to the reconstruction of an image, such that the radiation exposure of the patient is approximately 6% of the radiation dose applied in total.

Given the use of a detector with $Z=128$ lines and a line width of $B=0.6$ mm, the proportion of the leading movement and the trailing movement in the entire scan would increase to approximately 77%, such that the additional radiation exposure of the patient increases to approximately 39% of the radiation dose applied overall.

SUMMARY OF THE INVENTION

An object of the present invention is to provide a diaphragm device for an x-ray apparatus for scanning a subject, and a method for scanning a subject with such a diaphragm device, that allow scanning of a volume of the subject with a reduced radiation exposure composed to the conventional situation described above.

The invention proceeds from the insight that the radiation exposure of a subject can be reduced when both a very precise adjustment of the radiation beam for exposure of the measurement field of a detector and a dynamic masking of an unneeded portion of the x-ray radiation are implemented with the diaphragm device.

Two very different requirements, however, must be satisfied for the adjustment of a radiation beam on the measurement field of the detector and for dynamic masking of an unneeded portion of the radiation beam. The adjustment of the radiation beam on the measurement field of the detector must ensue very precisely with an adjustment precision of the diaphragm of a few micrometers. This high requirement results from the fact that, due to the high image scale (magnification), a slight position error of the diaphragm leads to the situation that the radiation beam being significantly displaced on the detector. In competition with this need is the necessity of the dynamic masking of the portion of the radiation beam being implemented with a high speed.

A precise and, at the same time, fast adjustment of the radiation beam can be achieved only insufficiently with known diaphragm devices, due to these very different requirements. An optimization of one of these requirements is possible only at the cost of the other requirement. To achieve a faster masking possibility, the diaphragm device would exhibit tolerances that would be too high for the precise adjustment of the radiation beam on the measurement field of the detector. Conversely, for achieving precise adjustment, the diaphragm device would exhibit an inertia that would be too high for dynamically masking the radiation beam. Conventional diaphragm devices therefore are normally operated such that, when in doubt, a larger region of the subject is exposed than would be necessary for reconstruction so that an artifact-free reconstruction of an image is ensured. In this case, however, the subject is exposed to an increased radiation exposure.

The invention furthermore is based on the insight that an acquisition of the projections necessary for reconstruction of an artifact-free image with optimally-low radiation exposure of the subject is possible when the adjustment of the radiation beam on the measurement field of the detector, and the dynamic masking of the unneeded portion of the radiation beam, are effected separately from one another.

According to the invention, the diaphragm device therefore has at least two diaphragms, with the radiation beam that has been adjusted with the first diaphragm being at least partially, dynamically masked by the second diaphragm for at least one segment of the scan of the subject.

The adjustment and the dynamic masking of the radiation beam thus ensues with two different diaphragms that are separate from one another, so that the different requirements for scanning a subject with a low radiation exposure can be simultaneously fulfilled. The first diaphragm is used for precise adjustment of the radiation beam on the measurement field of the detector, while the second diaphragm enables the dynamic masking of the radiation beam. By this separation, each diaphragm thus can be adapted in a safer and simpler manner to the function associated with it. The diaphragms are designed such that the adjustment of the radiation beam by the first diaphragm can be implemented with a high adjustment precision and the dynamic masking by the second diaphragm can be implemented with a high adjustment speed.

As a result of the dynamic masking of the radiation beam, the remaining radiation beam exposes essentially only a region of the subject that contributes to the reconstruction of an image, so that an unnecessary radiation exposure of the subject is avoided.

The segment of the scan in which the dynamic masking of the radiation beam ensues advantageously corresponds to a leading movement of the scan (for example in the form of a spiral scan) of the subject. Likewise, it is naturally also possible for the segment of the scan to correspond to a trailing movement of the scan of the subject. As already mentioned, the radiation exposure of the subject can be reduced to a significant degree by a dynamic masking in the leading movement and in the trailing movement during, for example, a spiral scan.

In an embodiment of the invention, the dynamic masking ensues dependent on a scan position in the direction of a system axis of the x-ray apparatus. It is also possible to control the masking dependent on the rotation angle of the acquisition system or dependent on a sample time.

Relative to the first diaphragm, the second diaphragm preferably is closer to the focus of the radiation beam. Due to the fan geometry of the radiation beam, positioning the second diaphragm closer to the focus of the radiation is advantageous because the transmission ratio between an adjustment of the second diaphragm and the change of the radiation beam cause thereby is increased. Nevertheless, reverse order of the diaphragm positions is also possible.

In an embodiment of the invention, both diaphragms of the diaphragm device are designed such that they can be adjusted in parallel with one another, such that a situation-dependent adaptation of the diaphragm device to the ray geometry of the acquisition system of the x-ray apparatus can be effected. An adaptation to beam geometry can be necessary, for example, when the focus of the radiator shifts due to thermal loads.

DESCRIPTION OF THE DRAWINGS

FIG. 6 is a diagram showing a parallel adjustment of both diaphragms.

DESCRIPTION OF THE PREFERRED EMBODIMENTS

Figure 1:
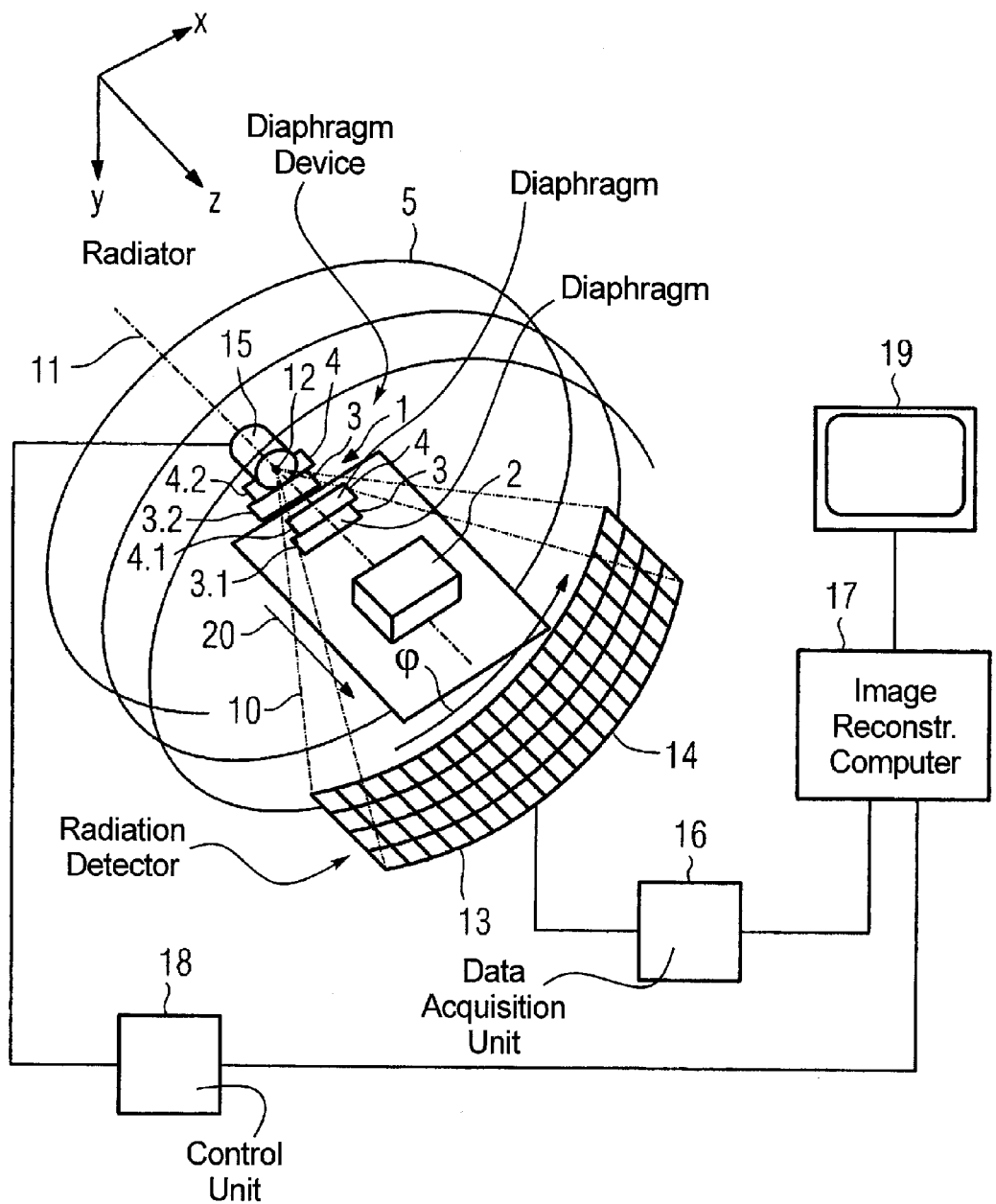
FIG. 1 is a perspective partial view, of a computed tomography apparatus with an inventive diaphragm device with two diaphragms.

An x-ray apparatus (here a computed tomography apparatus) is shown in FIG. 1. The acquisition system thereof includes a radiator 15 (for example in the form of an x-ray tube) with a source-proximate diaphragm device 1 and a mediation detector 13 fashioned as a laminar array. The array has a number of detector elements 14 arranged in rows and columns, with only one thereof being provided with a reference character.

The radiator 15 and the detector 13 are mounted opposite one another in a rotary frame (not explicitly drawn, known as a gantry) such that a fan-shaped radiation beam 10 emanating from a focus 12 of the radiator 15 in the operation of the computed tomography apparatus and masked by the diaphragm device 1, strikes the detector 13. The detector elements 14 generate respective attenuation value dependent on the attenuation of the radiation passing through the measurement region, each attenuation value being designated as a measurement value in the following. The translation of the radiation into measurement values ensues, for example, by means of a photodiode optically coupled with a scintillator, or by means of a directly-converting semiconductor. A set of measurement values of the detector 13 is known as a projection.

By means of a drive device (not shown) controlled by a control unit 18, the rotary frame can be set in rotation around a system axis 11 in the shown ω-direction. In this manner, a number of projections of a subject 2 located in the measurement region of the acquisition system can be produced from different projection directions. By rotation of the gantry with simultaneous, continuous feed of the subject 2 in the direction of the system axis 11, an examination volume of the subject 2 can be scanned that is larger than that of the measurement region formed by the acquisition system. The measurement values of the projections are read out from a data acquisition unit 16 and supplied to a computer 17 for calculation of a reconstructed image. The reconstructed image can be visually displayed to operating personnel on a display unit 19.

Figure 2:
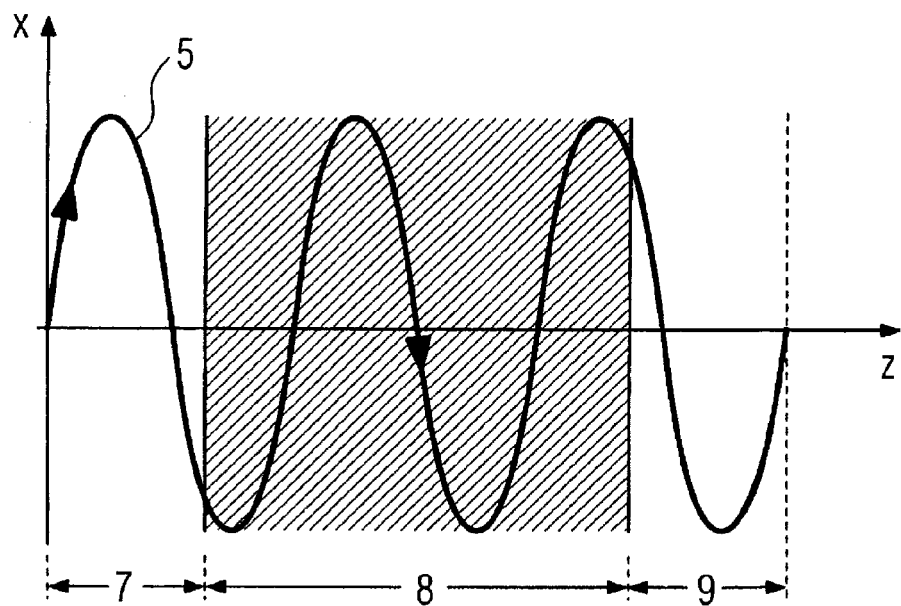
FIG. 2 is a diagram of a two-dimensional projection perpendicular to the system axis, showing a helical scan during the leading movement, the scan of the usable volume, and the trailing movement.

For reconstruction of an image of an examination volume (designated in the following as a usable volume 8), it is necessary to expose a sample volume that is larger than the usable volume 8 in the direction of the system axis 11. The larger (in comparison with the usable volume 8) sample volume essentially depends on the algorithm used for reconstruction of the image. It results from the number of the additionally-required rotations that must be implemented during a leading movement 7 (shown in FIG. 2) and trailing movement 9 of the helical scan 5 during reconstruction.

Without dynamic masking of a portion of the radiation beam 10 emanating from the radiator 15, during the leading movement 7 and the trailing movement 9, regions of the subject 2 are irradiated that do not contribute to the reconstruction of the image, causing the subject 2 (for example a patient) to be exposed to an unnecessary radiation exposure due to x-ray radiation during these segments of the helical scan 5.

To reduce the radiation exposure of the subject 2 in a scan procedure, the diaphragm device 1 has two different diaphragms 3 and 4. The first diaphragm 3 serves for precise adjustment of the radiation beam 10 on the measurement field of the detector 13. The first diaphragm 3 is designed such that the adjustment of the radiation beam 10 is possible with a very high adjustment precision. By contrast, the second diaphragm 4 serves for dynamic masking of the portion of the radiation beam 10 that is not needed for reconstruction. For example, the dynamic masking of the radiation beam 10 ensues during the leading movement 7 and the trailing movement 9 of the scan. The second diaphragm 4 is designed such that a particularly high adjustment speed can ensue, for example at multiple cm per second.

The adjustment and the masking of a portion of the radiation beam 10 are thus implemented separate from one another, such that the respective diaphragms 3 and 4 can be adapted to the appropriate requirements with regard to the adjustment precision and the adjustment speed.

Relative to the first diaphragm 3, the second diaphragm 4 is located closer to the focus 14, such that large alterations of the fan geometry can be made with slight adjustments of the second diaphragm 4. In principle, diaphragm devices can naturally also be realized with a reverse arrangement of the diaphragms.

Figure 3:
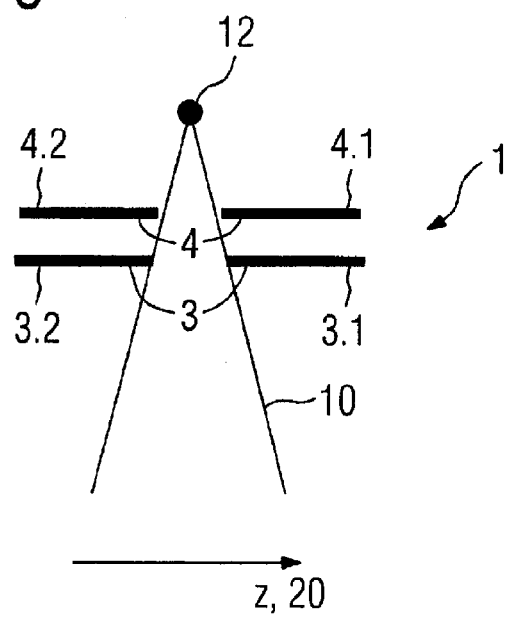
FIG. 3, in a lateral detail view, shows the diaphragm device shown in FIG. 1.

As shown in FIG. 3 in a lateral detail view of the diaphragm device 1, the diaphragm 3 has two diaphragm elements 3.1, 3.2 and the diaphragm 4 has two diaphragm elements 4.1, 4.2. In each of the diaphragms 3 and 4, the diaphragm elements thereof can be adjusted independently of one another so as to gate the radiation beam 10.

The movement of the diaphragm elements 3.1, 3.2 and 4.1, 4.2 can also ensue synchronously, particularly when slit diaphragms with a fixed opening are used. Also, only one of the two diaphragms 3 or 4 can be a slit diaphragm, and the other diaphragm can be designed with two diaphragm elements that can be adjusted independent of one another.

The diaphragm elements 3.1, 3.2 of the first diaphragm 3 are, as just described, executed such that they can be adjusted, such that a very precise adjustment of the radiation beam 10 to the measurement field of the detector 13 can ensue. For example, each of these diaphragm elements 3.1, 3.2 can interact with an adjustment motor provided for this purpose, the adjustment motor exhibiting an adjustment precision of a few micrometers. Conventionally, the high adjustment precision is achieved at the cost of a fast dynamic adjustment of the diaphragm elements. For this reason, the first diaphragm 3 is not suited for dynamic masking of a portion of the radiation beam 10 in the region of the leading movement 7 and the trailing movement 9 of the helical scan 5. In these regions, predominantly fast adjustment speeds of multiple centimeters per second (depending on the operating mode of the computed tomography apparatus) are required to prevent the radiation exposure of the subject 2.

For fast dynamic masking of a corresponding portion of the radiation beam 10, the additional second diaphragm 4 (which can be operated independently of the first diaphragm 3) is used. The high adjustment speed of multiple centimeters per second of the second diaphragm 4 is achievable, for example, by the use of corresponding adjustment motors that interact with the diaphragm elements 4.1, 4.2. The high adjustment speed of the second diaphragm 4 can also lead to larger tolerances of the adjustable precision of the adjustment position of the diaphragm elements 4.1, 4.2. For this reason, the second diaphragm 4 is operated such that the masking of the radiation beam 10 to reduce the radiation exposure ensues by taking the possible tolerances into account, such that at each point in time the sub-region of the detector 13 necessary for reconstruction is exposed during the leading movement 7 and the trailing movement 9.

Figure 4:
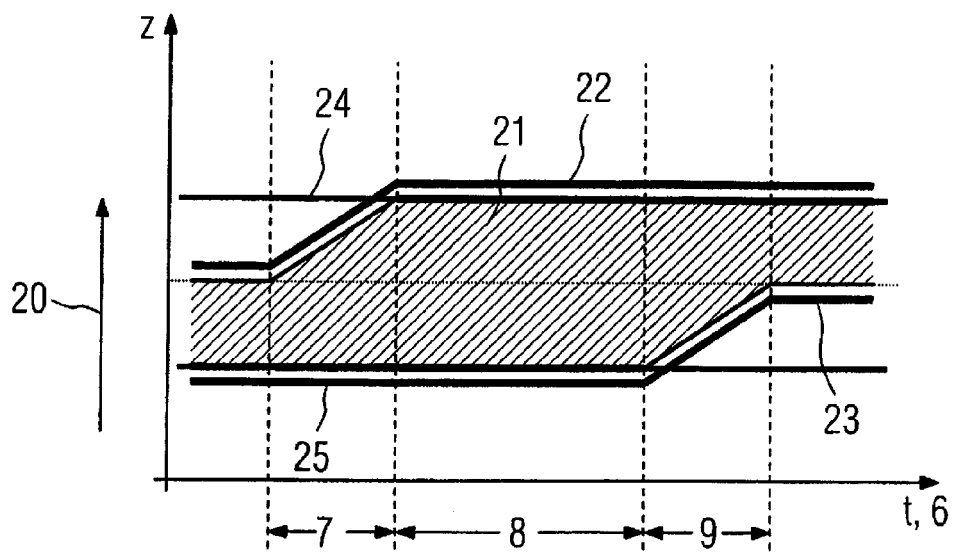
FIG. 4 is a diagram showing the adjustment positions of the diaphragm elements of both diaphragms relative to the gantry during the leading movement, the scan of the usable volume, and the trailing movement.

FIG. 4 illustrates the interaction of both diaphragms 3 and 4 during the helical scan 5 of the subject 2, wherein the adjustment positions 22, 23, 24, 25 of the respective diaphragm elements in the direction of the system axis 11 of the computed tomography apparatus during the leading movement 7, the scan of the usable volume 8, and the trailing movement 9 are shown relative to the gantry in the form of a diagram. The adjustment positions of the first diaphragm element 3.1 of the first diaphragm 3 are provided with the reference character 24; those of the second diaphragm element 3.2 are provided with the reference character 25. The adjustment positions of the first diaphragm element 4.1 of the second diaphragm 4 are provided with the reference character 22; those of the associated second diaphragm element 4.2 are provided with the reference character 23. Moreover, the aperture region 21 of the diaphragm device, which is required for an artifact-free reconstruction of an image, is shown hatched.

The first diaphragm 3 is adjusted before the beginning of the examination in a precise manner such that the entire measurement field of the detector 13 can be exposed. Typically no adjustment of the first diaphragm 3 ensues during the examination, under the condition that the geometry of the acquisition system, in particular the geometry between focus 12 and detector 13, does not change. The adjustment positions 24, 25 of the two diaphragm elements 3.1, 3.2 of the first diaphragm 3 are thus constant during the course of the examination, as shown in FIG. 4.

As can be seen from the hatched aperture region 21, the complete region of the diaphragm aperture of the first diaphragm 3 is not used for reconstruction of the image during the leading movement 7; but only a sub-region of this is used. In this example, at the beginning of the scan the sub-region amounts to approximately half of the entire diaphragm aperture of the first diaphragm 3. The sub-region used for reconstruction increases in line with the subject feed 20 and, given scanning of the usable volume 8, achieves the entire size of the diaphragm aperture of the first diaphragm 3, which is adjusted such that the entire measurement field of the detector 13 is exposed in a very precise manner. Reversed, in this example the used diaphragm aperture shrinks again with the subject feed 20 to approximately half of the diaphragm aperture of the first diaphragm 3.

The second diaphragm 4 is dynamically adjusted to reduce the radiation exposure during the leading movement 7, such that the unneeded part of the radiation beam 10 is essentially masked.

The masking is effected by means of the first diaphragm element 4.1 of the second diaphragm 4. In the exemplary embodiment described here, at the beginning of the examination this diaphragm element 4.1 is extended in the direction of the system axis 11 until approximately half of the diaphragm aperture of the first diaphragm 3 is covered and the unneeded part of the radiation beam 10 is masked. During the leading movement 7 of the scan, the first diaphragm element 4.1 is continuously backed up inline with the subject feed 20, whereby during the leading movement 7 the first diaphragm element 4.1 of the second diaphragm 4 is stationary relative to the subject 2 and only the sub-region of the measurement field that is necessary for reconstruction is irradiated.

In order to allow for the possible poorer adjustment precision of the second diaphragm 4, the adjustment positions of this diaphragm element 4.1 are selected such that in each case the sub-region of the measurement field of the detector 13 that is necessary for reconstruction is exposed even given greater occurring tolerances. The second diaphragm 4 is thus set back by a small amount further than this would normally be necessary. The adjustment position of the second diaphragm element 4.2 of the second diaphragm 4 is selected during the leading movement 7 such that the radiation beam 10 is delimited by the precisely set second diaphragm element 3.2 of the first diaphragm 3.

In the region (subsequent to the leading movement 7) of the scan for acquisition of the usable volume 8, both diaphragm elements 4.1, 4.2 of the second diaphragm 4 are moved back so that the radiation beam 10 is merely faded in by the first diaphragm 3 in a precise manner.

Only upon the trailing movement 9 of the scan is the second diaphragm element 4.2 of the second diaphragm 4 moved (inline with the subject feed 20) into the diaphragm aperture formed by the first diaphragm 3, such that the portion of the radiation beam 10 that is not needed for reconstruction is dynamically masked. During the trailing movement 9, the second diaphragm element 4.2 of the second diaphragm 4 is thus aligned stationary relative to the subject. Due to the lesser adjustment precision of the second diaphragm 4, adjustment positions, as in the leading movement 7 adjustment positions are taken in which in each case the sub-region of the measurement field necessary for reconstruction is exposed even given greater tolerances in the respectively-adopted position.

In this exemplary embodiment, the adjustment positions of the diaphragm elements 4.1, 4.2 that are adopted at the beginning of and during the scan in the leading movement 7 and in the trailing movement 9 to reduce the radiation exposure are only examples and significantly depend on which algorithm is used for reconstruction.

Figure 5:
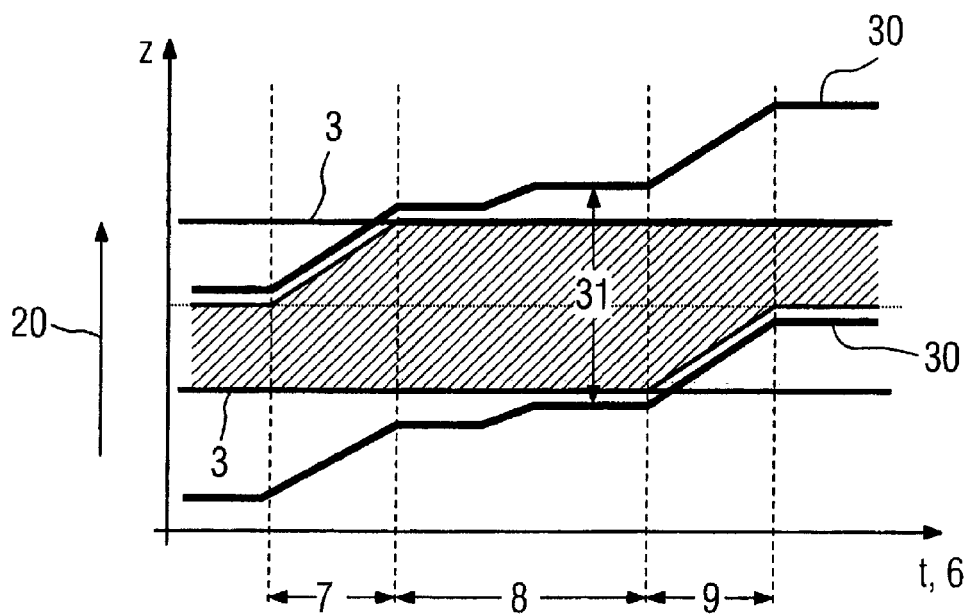
FIG. 5 is a diagram showing the adjustment positions of both diaphragms relative to the gantry during the leading movement, the scan of the usable volume, and the trailing movement, wherein the second diaphragm is a slit diaphragm.

Deviating from the above example, it is also possible for at least one of the two diaphragms 3 or 4 to be a slit diaphragm 30 with a fixed set diaphragm aperture 31. FIG. 5 exemplarily shows the interaction of the two diaphragms during a scan for the case that the second diaphragm is executed as a slit diaphragm 30. In this case, the dynamic masking of the unneeded portion of the radiation beam 10 ensues via an adjustment of the slit diaphragm 30 as a whole. The diaphragm aperture 31 of the slit diaphragm 30 is dimensioned such that, in the region of the scan of the usable volume 8, the delimitation of the radiation beam 10 is possible solely via the first diaphragm 3. If the diaphragm aperture 31 of the slit diaphragm 30 is greater than that of the first diaphragm 3, as shown in the example, the slit diaphragm 30 is adjusted during the scan of the usable volume 8 such that a dynamic delimitation of the radiation beam 10 during the trailing movement 9 is possible with the opposite (with regard to the leading movement 7) part of the slit diaphragm 30.

During the operation of the computed tomography apparatus, the thermal load of the radiator 15 can lead to the focus 12 being shifted from its original position. For this reason it can be necessary to correct the position of both diaphragms 3 and 4. For this purpose, both diaphragms 3, 4 as depicted in FIG. 6 can be adjusted in parallel with one another, with the displacement being implemented corresponding to the shift of the focus 12 of the radiation. The displacement is possible, for example, by mounting both diaphragms 3 and 4 on a rail system.

Although modifications and changes may be suggested by those skilled in the art, it is the intention of the inventor to embody within the patent warranted hereon all changes and modifications as reasonably and properly come within the scope of his contribution to the art.

I claim as my invention:

1. A diaphragm device for gating a moving x-ray beam in an x-ray apparatus having a radiation detector on which the x-ray beam is incident, said diaphragm device comprising:

at least two diaphragms, each disposed to interact with said moving x-ray beam during a scan of a subject;

a control unit that operates a first of said at least two diaphragms to gate said x-ray beam to define an area extent of said x-ray beam that is substantially unchanging during said scan, and that operates a second of said at least two diaphragms to dynamically mask at least a portion of said area extent relative to said radiation detector dependent on movement of said x-ray beam during the scan.

2. A diaphragm device as claimed in claim 1 wherein said control unit operates said first of said at least two diaphragms to gate said x-ray beam with a high adjustment precision and operates said second of said at least two diaphragms to dynamically mask said area extent of said x-ray beam with a high adjustment speed.

3. A diaphragm device as claimed in claim 1 wherein said x-ray beam emanates from a focus, and wherein said second of said at least two diaphragms is disposed closer to said focus than said first of said at least two diaphragms.

4. A diaphragm device as claimed in claim 1 comprising an adjustment mechanism operated by said control unit that adjusts said first of said at least two diaphragms and said second of said at least two diaphragms in parallel with each other.

5. A diaphragm device as claimed in claim 1 wherein at least one of said first of said at least two diaphragms and said second of said at least two diaphragms comprises adjustable diaphragm elements.

6. A diaphragm device as claimed in claim 1 wherein at least one of said first of said at least two diaphragms and said second of said at least two diaphragms is a slit diaphragm.

7. An x-ray examination apparatus for scanning a subject, comprising:

an x-ray source that emits an x-ray beam emanating from a focus;

a radiation detector disposed in a path of said x-ray beam, said x-ray source and said radiation detector being configured to receive a subject therebetween and being movable to conduct a scan of the subject with said x-ray beam, thereby also producing movement of said x-ray beam during said scan;

a diaphragm device disposed in said path of said x-ray beam preceding the subject, said diaphragm device comprising at least two diaphragms each disposed to interact with the moving x-ray beam during said scan; and a control unit that operates a first of said at least two diaphragms to define an area extent of said x-ray beam, that is substantially unchanging during said scan, and that operates a second of said at least two diaphragms to dynamically mask a portion of said area extent of said x-ray beam, relative to said radiation detector, dependent on the movement of the x-ray beam during the scan.

8. An x-ray examination apparatus as claimed in claim 7 wherein said x-ray source and said radiation detector are movable to conduct a spiral scan of the subject, as said scan of the subject.

9. An x-ray examination apparatus as claimed in claim 7 wherein said diaphragm device comprises a first adjustment mechanism that is operated by said control unit to adjust said first of said at least two diaphragms with a high adjustment precision, and a second adjustment mechanism that is operated by said control unit to adjust said second of said at least two diaphragms with a high adjustment speed.

10. An x-ray examination apparatus as claimed in claim 7 comprising an image reconstruction computer that receives attenuation data from said radiation detector and that calculates an image of the subject from said attenuation data using a reconstruction algorithm, and wherein said control unit operates said first of said at least two diaphragms to define said area extent of said x-ray beam so that said x-ray beam irradiates only a region of the subject that contributes to reconstruction of said image in said reconstruction algorithm.

11. An x-ray examination apparatus as claimed in claim 7 wherein said scan comprises a leading movement, and wherein said control unit operates said first of said at least two diaphragms to gate said x-ray beam during said leading movement of said scan.

12. An x-ray examination apparatus as claimed in claim 7 wherein said scan comprises a trailing movement, and wherein said control unit operates said first of said at least two diaphragms to gate said x-ray beam during said trailing movement of said scan.

13. An x-ray examination apparatus as claimed in claim 7 comprising a system axis, and wherein said control unit operates said second of said at least two diaphragms to dynamically mask said x-ray beam dependent on a position in said scan in a direction of said system axis.

14. An x-ray examination apparatus as claimed in claim 7 wherein said second of said at least two diaphragms is disposed closer to said focus than said first of said at least two diaphragms.

15. An x-ray examination apparatus as claimed in claim 7 wherein said diaphragm device comprises an adjustment mechanism that is operated by said control unit to adjust said first of said at least diaphragms and said second of said at least two diaphragms in parallel with each other.

16. An x-ray examination apparatus as claimed in claim 7 wherein at least one of said first of said at least two diaphragms and said second of said at least two diaphragms comprises adjustable diaphragm elements.

17. An x-ray examination apparatus as claimed in claim 7 wherein at least one of said first of said at least two diaphragms and said second of said at least two diaphragms is a slit diaphragm.

18. A method for scanning a subject with an x-ray beam, comprising the steps of:

emitting an x-ray beam from a focus of an x-ray source;

moving said x-ray source and a radiation detector disposed in a path of said x-ray beam, with a subject therebetween, to conduct a scan of the subject with said x-ray beam, thereby also moving said x-ray beam;

disposing a diaphragm device in a path of said x-ray beam preceding said subject, said diaphragm device comprising at least two diaphragms; and automatically adjusting a first of said at least two diaphragms to define an area extent of said x-ray beam that is substantially unchanging during said scan, and automatically operating a second of said two diaphragms to dynamically mask a portion of said area extent of said x-ray beam, relative to said radiation detector, dependent on the movement of the x-ray beam during the scan.

19. A method as claimed in claim 18 comprising moving said x-ray source and said radiation detector to conduct a spiral scan of the subject, as said scan.

20. A method as claimed in claim 18 comprising, in said diaphragm device, adjusting said first of said at least two diaphragms with a high adjustment precision, and adjusting said second of said at least two diaphragms with a high adjustment speed.

21. A method as claimed in claim 18 comprising computationally reconstructing an image of the subject from attenuation data from the radiation detector using a reconstruction algorithm, and comprising, with said first of said at least two diaphragms, defining said area extent of said x-ray beam so that said x-ray beam irradiates only a region of the subject that contributes to reconstruction of said image in said reconstruction algorithm.

22. A method as claimed in claim 18 wherein said scan comprises a leading movement, and comprising, with said first of said at least two diaphragms, gating said x-ray beam during said leading movement of said scan.

23. A method as claimed in claim 18 wherein said scan comprises a trailing movement, and comprising, with said first of said at least two diaphragms, gating said x-ray beam during said trailing movement of said scan.

24. A method as claimed in claim 18 comprising conducting said scan around a system axis, and comprising, with said second of said at least two diaphragms, dynamically masking said x-ray beam dependent on a position in said scan in a direction of said system axis.

25. A method as claimed in claim 18 comprising placing said second of said at least two diaphragms closer to said focus than said first of said at least two diaphragms.

26. A method as claimed in claim 18 comprising adjusting said first of said at least diaphragms and said second of said at least two diaphragms in parallel with each other.

* * * * *